United States Patent [19]

Curtis et al.

[11] Patent Number: 5,098,291
[45] Date of Patent: Mar. 24, 1992

[54] PRESSURIZED MEDICANT APPLICATOR

[75] Inventors: John P. Curtis, Bloomsbury; James H. Kemp, Piscataway, both of N.J.

[73] Assignee: Colgate-Palmolive Company, Piscataway, N.J.

[21] Appl. No.: 452,025

[22] Filed: Dec. 18, 1989

Related U.S. Application Data

[63] Continuation-in-part of Ser. No. 338,259, Apr. 14, 1989, Pat. No. 4,958,751.

[51] Int. Cl.$^5$ .................... A61C 5/04; B65D 83/20
[52] U.S. Cl. ........................... 433/89; 433/88; 433/80; 222/402.13
[58] Field of Search ............... 433/80, 82, 85, 87, 433/88, 89; 128/66, 62 A; 222/402.13

[56] References Cited

U.S. PATENT DOCUMENTS

| | | | |
|---|---|---|---|
| 1,681,320 | 8/1928 | Bergl | 128/62 A |
| 2,645,097 | 7/1953 | Posch | 433/89 |
| 3,144,867 | 8/1964 | Trupp et al. | 128/234 |
| 3,164,153 | 1/1965 | Zorzi | 128/224 |
| 3,189,232 | 6/1965 | Joffe | 222/402.13 |
| 3,391,696 | 7/1968 | Woodward | 128/232 |
| 3,612,706 | 10/1971 | Verga | 401/190 |
| 3,742,942 | 7/1973 | Westline | 128/62 A |
| 4,236,889 | 12/1980 | Wright | 433/86 |
| 4,457,711 | 7/1984 | Maloney et al. | 433/82 |
| 4,512,769 | 4/1985 | Kozam et al. | 604/209 |
| 4,655,198 | 4/1987 | Hommann | 128/66 |
| 4,906,187 | 3/1990 | Amadera | 433/80 |

FOREIGN PATENT DOCUMENTS

| | | | |
|---|---|---|---|
| 143617 | 6/1985 | European Pat. Off. | 433/80 |
| 3203723 | 8/1983 | Fed. Rep. of Germany | 433/89 |

*Primary Examiner*—John G. Weiss
*Attorney, Agent, or Firm*—Michael J. McGeal; Murray M. Grill; Robert C. Sullivan

[57] ABSTRACT

This hand-held pressurized applicator is very effective to apply medicants to the perio pocket area of the toothgum margin. This pressurized applicator can be held and used in any orientation. The medicant is applied at a pressure of greater than about 20 psi, and preferably a pressure of greater than about 30 psi. In one embodiment, there is used a tip that fits into the perio pocket of teeth, and in a second embodiment there is used a toothbrush with the medicant flowing from between the bristles of the toothbrush or through hollow bristles.

15 Claims, 2 Drawing Sheets

PRESSURIZED MEDICANT APPLICATOR

This application is a continuation-in-part of our application Ser. No. 338,259, filed Apr. 14, 1989, now U.S. Pat. No. 4,958,751.

This invention relates to a hand-held pressurized applicator for applying medicants and other substances to the oral cavity. More particularly, this invention relates to a hand-held pressurized applicator for applying medicants to one's teeth and to the margin between the gums and teeth.

A primary problem today in the area of oral care is periodontitis. This results from the formation of bacterial from food debris and the like which is not promptly removed from the mouth, and in particular from the tooth and gum areas. Brushing, even after each meal, is not effective for removing all of the food debris. One reason is that brushing alone cannot reach all of the areas of the oral cavity where food debris can collect. Proper dental flossing will improve the degree of cleaning of one's teeth, however even with good brushing and flossing, it is not possible to totally clean around orthodontic or prosthetic appliances. Further, these various techniques for cleaning one's teeth are not effective for removing food debris and other materials from the gum-tooth margin which is also termed the periodontal pocket area. When a person is eating, pieces of food can become lodged in the gum-tooth margin area. This results from the pressure of chewing and biting and the condition of the tooth-gum margin.

There is thus a need for improved personal care of a person's mouth. It is possible to regularly visit a dentist or dental technician and have one's mouth thoroughly cleaned. However, this is both expensive and time consuming. Now, a device has been developed which assists a person in better maintaining their mouth, and in particular the interstitial tooth areas and the tooth-gum margin area. This present device can very advantageously be utilized for cleaning and medicating the periodontal pocket areas, the tongue, teeth, and ones throat. There is provided a relatively easy to operate device which can be used to very effectively flush debris from the periodontal pockets and also to provide a medication to the periodontal pocket areas. This cleaning and medicating device is compact, easy to handle, can be used in essentially any orientation, and can be used to deliver a variety of different substances. This pressurized applicator is very effective in flushing and cleaning both shallow and deep periodontal pockets. In this way, it is able to remove bacteria, any residue, epithelial matter and any carotic accretions. Since this device is lightweight and can be operated using one hand, it is possible for a person to accurately maintain the device in position and to thoroughly clean their periodontal pocket areas. Further, it is possible to quickly and easily change from the use of one medicant or other substance to another.

Various devices have been developed over the years for providing techniques for cleaning between one's teeth and for cleaning the gum-tooth margin area, that is the periodontal pockets. Some of the devices that have been developed can be used by an individual in their personal oral care program. However, other devices require the assistance of another person, and are primarily directed for use by dental professionals. In U.S. Pat. No. 3,144,867, there is disclosed a pump device which is utilized for cleaning areas of a person's mouth as well as for the delivery medicants. This device comes equipped with various shaped tips which can be inserted between teeth as well as into the periodontal pocket areas. The objective is to flush the periodontal pocket areas of food debris and other materials. However, since this device is pressurized by means of a hand pump, there are the problems of maintaining a sufficiently high enough pressure in order to properly clean the periodontal pocket areas and to also maintain the tip of the device in the periodontal pocket areas. A problem with manual pump devices is that as the device is pumped, there is a tendency for the tip to be dislodged from the periodontal pocket area into which it has been inserted. This is the result of having to both hold the device and to put pressure on a spring loaded trigger in order to provide for a pumped stream of liquid. This device, although useful in enhancing a person's care of their teeth and gums, is not highly effective for inclusion in a person's personal health care program.

In U.S. Pat. No. 3,164,153, there is disclosed a device for the cleaning and rinsing of a person's teeth prior to the application of sealants or other treatments. This is a pressurized device which is utilized by a dental practitioner in preparing a patient for further dental treatment. This device is generally interesting but would not be useful for use in conjunction with a person's personal dental care program.

U.S. Pat. No. 3,391,696 discloses a manually operated, dental hygiene, liquid pressure device. The function of this device is to remove food debris and other materials from around a person's teeth and also to provide stimulation to the gums. This is accomplished by squeezing the reservoir area of the device to thereby force the contained liquid upwardly and out through a small tip which can be placed between a person's teeth and also along the gum line. This device is effective for cleaning around orthodontic and prosthetic appliances, but is not effective with regard to cleaning deep and shallow periodontal pocket areas. One problem with regard to this device is the need to manually squeeze the device. If it were attempted to utilize this device for cleaning periodontal pockets, it would be difficult to maintain the tip within a periodontal pocket area while the liquid reservoir was being squeezed.

U.S. Pat. No. 4,236,889 discloses a hand held dental cleaning device. This is a battery operated device. In this device, there is enclosed in the handle area an electric motor, pump and a battery source of power. In an upper part of the device leading to a neck region is a reservoir for the liquid that is to be utilized in the dental cleaning operation. A problem with this device, besides its rather high cost, is the weight and bulk due to the need for there to be contained within the device an electric motor, a pump and a battery source of power. This causes the device to be larger than is necessary as well as to be heavier than is necessary. A resulting consequence is that the device is difficult to handle. Further, it is not possible to readily change the liquid that is being utilized for the dental cleaning operation.

U.S. Pat. No. 4,457,711 is directed to a pressurized oral spraying device. The objective of this device is to provide a spray or mist into one's mouth. This device is self operated and is used as a part of a person's personal dental care regiment. The primary objective in the use of this device is to remove various hard substances from teeth and gums as well as to provide for a hygienic flushing of the full mouth cavity. This device would not be effective for cleaning deep or shallow periodontal pockets.

U.S. Pat. No. 4,512,769 discloses a manually operated syringe device for flushing periodontal pockets and other soft tissue spaces. The objective here is to provide a technique for removing food fragments and other materials from the periodontal pocket area. Through the hand operation of this syringe, there is provided a pressurized stream of liquid that can be flowed into the periodontal pocket areas through the shaped tip of the device. The drawbacks with regard to this device include the fact that the device is manually operated and thus difficult to maintain in the periodontal pocket area while pressure is being applied to manually operate the pumping mechanism. Further, in the design of this device, it is difficult to readily change the liquid which is being applied to the periodontal pocket area.

U.S. Pat. No. 4,655,198 discloses a hand held device that is to be utilized in a persons dental hygiene program. This device is primarily for use in flushing and irrigating parts of a person mouth. In this way, food debris and other similar substances can be removed from the oral cavity. This device is not directed to rinsing the shallow and deep periodontal pockets, nor for the application of medicants to the shallow and deep periodontal pockets.

A primary objective of the present invention is to provide a device which is compact, lightweight, of a low cost and which can be readily utilized in any orientation for flushing and cleaning deep and shallow periodontal pockets as well as for delivering medicants to the periodontal pocket area. Further, it is an objective for such a device that it be able to be quickly adapted to deliver different medicants and other substances to the periodontal pockets. This cannot be effectively accomplished utilizing the prior art devices.

BRIEF DESCRIPTION OF THE INVENTION

The present invention is directed to a hand-held device which can be effectively utilized for rinsing all areas of a person's mouth including the deep and shallow periodontal pocket areas of a person's mouth and for delivering a medicant or other substance to a person's teeth and/or gums including the deep and shallow periodontal pockets. The device is comprised of a body housing portion, a pressurized cartridge and a delivery conduit for flowing the substance contained in the pressurized cartridge into a person's mouth for treatment of the periodontal areas, teeth, gums, and other parts of the mouth. In addition, the cartridge can be readily inserted into or removed from the body housing of the device. By changing cartridges, it is possible to quickly change the substance that is to be delivered into the mouth cavity. In this way, the device can be utilized to deliver particular rinses and medicants into the deep and shallow periodontal pockets, and other substances onto the gums, teeth, tongue and other parts of the mouth. Further, due to the valve arrangement within the cartridge, it is possible to utilize the applicator through a 360 degree orientation. In essentially any orientation, the applicator will deliver a pressurized flow of liquid. The cartridges have a valve which is actuated by a trigger switch on the body housing of the device. On the applicator end of the device, there is either a rubber tip which is utilized for flowing a liquid rinse, medicant or other substance into the deep and shallow periodontal pockets, or a toothbrush head. When a toothbrush head is utilized, the substance from the cartridge can flow out through openings in the bristle area of the toothbrush head, or can flow out through hollow bristles. In this way a medicant or other substance can be delivered to the teeth, gums, or other parts of the mouth cavity.

DETAILED DESCRIPTION OF THE INVENTION

As has been noted, the present pressurized applicator device is a hand held unit which can easily be used by a person in their personal dental hygiene program. This pressurized applicator is lightweight, compact and easy to handle. Since the medicant or other substance that is to be dispensed is under pressure in a cartridge, there is not the problem of having to include a pumping mechanism, or with regard to the problem of manually pumping and trying to maintain the unit in a particular position. Further, due to the simplicity of the pressurized applicator and the ease with which pressurized cartridges can be inserted and removed from parts of the mouth, more than one medicant or other substance can be utilized in a person's oral hygiene program. It is only necessary when there is to be a change of medicant or other substance to quickly remove one pressurized cartridge and to insert another pressurized cartridge. Consequently, one type of medicant of other substance can be utilized to flush and to apply a medicant to the deep and shallow periodontal pockets, while a second medicant or substance can be utilized to treat the exterior surfaces of the gums as well as to treat any other problem within the oral cavity. There are yet other advantages. This pressurized applicator will be described in more detail with specific reference to the drawings.

Figure 1:
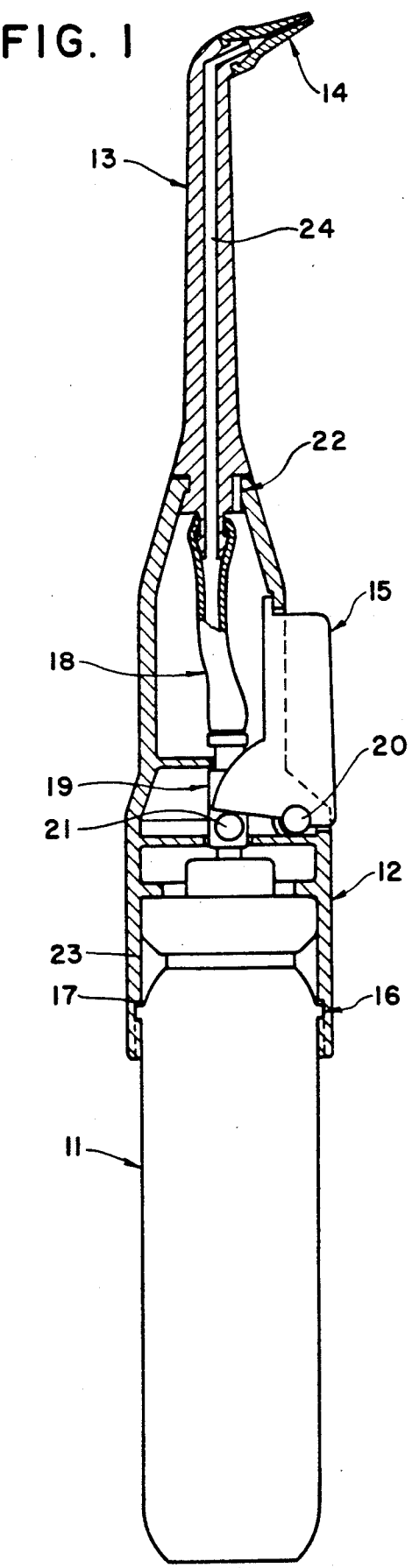
FIG. 1 is an elevational view in a section of the present applicator device showing the use of a tip for insertion into periodontal pockets.

FIG. 1 is an elevational view partially in section of the present pressurized applicator device. The pressurized applicator device 10 consists of body housing portion 12, pressurized cartridge 11 and delivery section 13. In this embodiment, delivery section 13 is shown as terminating in rubber tip 14 which can be utilized for flushing periodontal pockets as well as for providing medicants to periodontal pockets. The housing 12 at its lower end accepts the pressurized cartridge 11 and maintains this pressurized cartridge within the body housing. In this embodiment, the pressurized cartridge is shown as maintained within the body housing by means of a bayonet type of connection. This bayonet type of connection consists of projections 16 on the pressurized cartridge which fits into indents 17 on the body housing. The upper part of the pressurized cartridge fits into valve actuator 19. The valve which dispenses the pressurized medicant or other substance is preferably an integral part of the pressurized cartridge. This reduces the weight and complexity of the applicator. Extending upwardly from the pressurized cartridge is a dispensing conduit 31 which also functions as part of the valving system of the pressurized cartridge. The upper part of the valve actuator 19 is connected by flexible tubing 18 to the conduit 24 which extends through delivery section 13. The trigger 15 pivots on pin 20 and by being depressed causes the valve actuator 19 to move downwardly and to thus activate the valve in the pressurized cartridge. The trigger causes the valve actuator to move downwardly by contacting projecting arm 21 on the valve actuator. The pressure on the medicant or other substance contained in the pressurized cartridge will provide the force to return valve actuator 19 to its original position.

The valve actuator consists of a fitment which has a channel therethrough. On its lower end, there is an opening of a diameter to accept the dispensing conduit 31 of the pressurized cartridge. The channel is thus of a larger diameter in the lower end. Within the fitment, the channel decreases in diameter. The dispensing conduit abuts the ledge in the region of the diameter decrease. In this way, when the valve actuator is depressed downwardly, the ledge contacts the dispensing conduit to push the dispensing conduit downwardly and thus actuate the valve.

As is seen in this embodiment, the delivery conduit 24 will provide medicant or other substance to the rubber tip 14 which is shown here as an applicator of substances to periodontal pockets. The pressurized cartridges 11 will contain medicants or other substances at a pressure of greater than about 20 psi, and preferably at a pressure of greater than 30 psi. A most preferred pressure range for such substances is from about 30 psi to about 45 psi. Such pressures are desired in order to adequately flush the periodontal pocket areas and also for delivery of medicants into periodontal the pockets.

Figure 4:
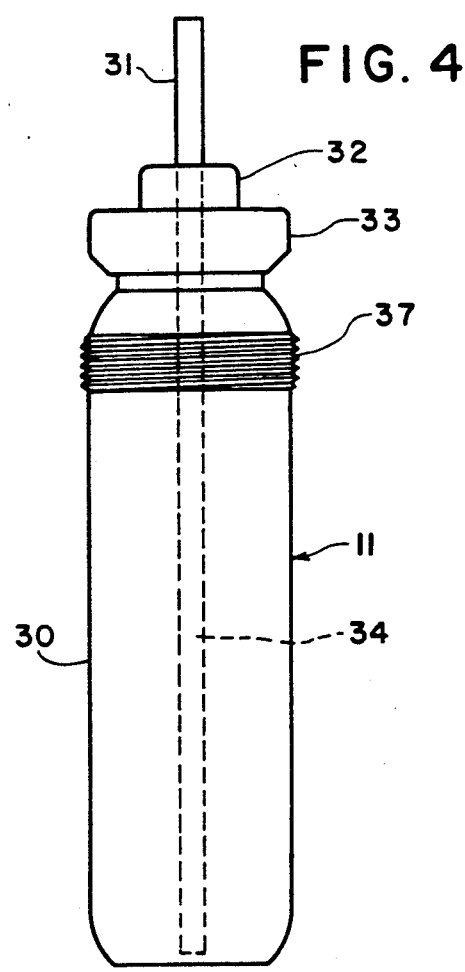
FIG. 4 shows a cartridge which has external threads and which can be utilized in conjunction with the body housing of FIG. 3.
Figure 2:
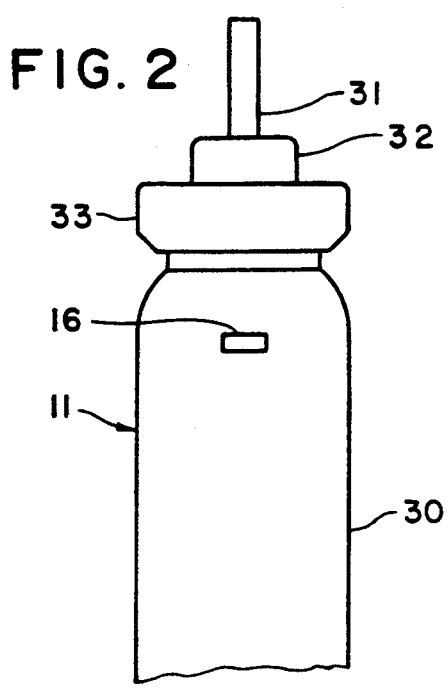
FIG. 2 is an elevational view of a cartridge showing means for attaching the cartridge to the body housing of the device.

FIG. 2 is an elevational view of a pressurized cartridge. The pressurized cartridge 11 has a transparent wall area 30. Projecting downwardly into the pressurized cartridge is dip tube 34 (as shown in FIG. 4) which is adapted to receive medicant or other substance from the pressurized cartridge. On the upper portion of the pressurized cartridge is dispensing conduit 31 for delivering the medicant or other substance from the pressurized cartridge. Projections 16 are utilized to maintain the pressurized cartridge within the body housing of the pressurized applicator. Within the next area 32 and 33 of the pressurized cartridge, there is the closure and the valve mechanism for delivery of the medicants or other substances from the pressurized cartridge. It is a feature of this pressurized cartridge that it can deliver medicant or other substances regardless of the orientation of the pressurized cartridge. That is, the position of the pressurized cartridge can vary through 360° and the medicant or other substances still be properly delivered as needed. In order to actuate the pressurized cartridge for the delivery of medicant or other substances, the dispensing conduit 31 is moved downwardly to thereby open the valve mechanism on the pressurized cartridge and to permit the delivery of the medicant or other substance. It is the valve actuator 19 that fits over dispensing conduit 31 and which when actuated by means of trigger 15 causes the stem 31 to move downwardly and thus to activate the valve mechanism in the neck areas of the pressurized cartridge.

Figure 2A:
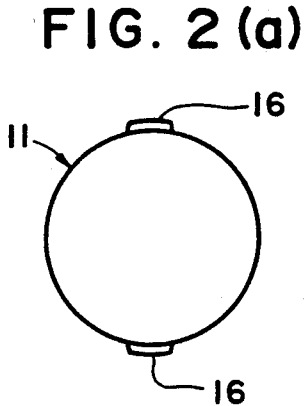
FIG. 2(a) is a view showing the projections on the cartridge.

In FIG. 2(a), the projections 16 on the cartridge are shown in more detail. A cartridge with projections 16 is used when a bayonet type of attachment of the cartridge to the applicator is desired.

Figure 3:
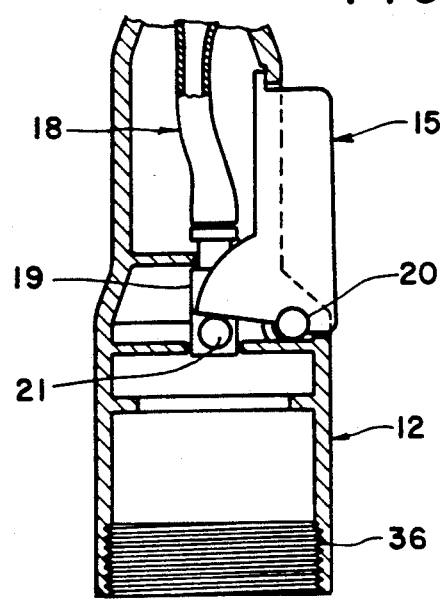
FIG. 3 is a sectional elevational view of the body housing and applicator means sections of the device showing a threaded section on the lower portion of the body housing which is adapted to receive a cartridge having external threads.

FIG. 3 is a further view of the body housing and the delivery section of the present pressurized applicator. However, in this embodiment, it is shown that the lower portion of the body housing is threaded and thus is adapted to receive a pressurized cartridge which has mating threads. The threads 36 of the body housing will mate with threads 37 on the pressurized cartridge of FIG. 4. Otherwise, this pressurized cartridge is the same as the pressurized cartridge of FIG. 2.

Figure 5:
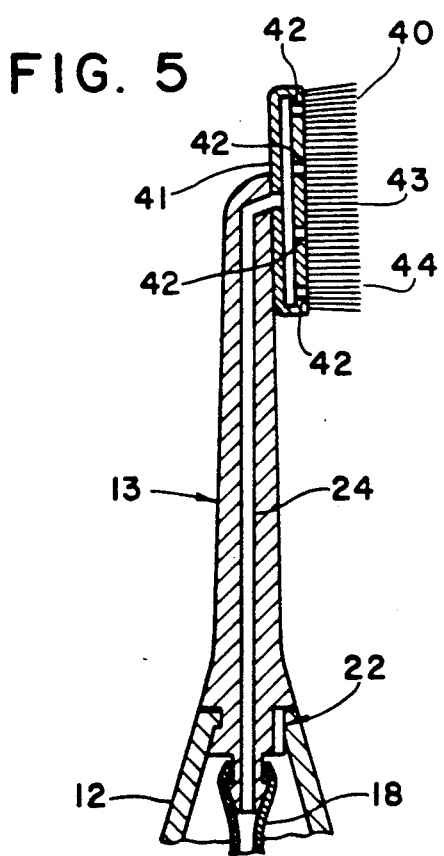
FIG. 5 is an elevational view in section showing the applicator device having a toothbrush head for the delivery of a medicant or other substance in place of the periodontal rubber tip.

FIG. 5 shows an embodiment of the present pressurized applicator wherein in place of the periodontal tip 14 there is a toothbrush 40. This toothbrush head is preferably a replaceable unit. In this way, brush heads can be interchanged, and the brush head can be replaced with a periodontal tip. This embodiment of the pressurized applicator functions in the same manner as that of FIG. 1 which has the periodontal tip 14 attached. In this embodiment, the medicant or other substance flows through conduit 24 to conduit 41 in the toothbrush head 40. From conduit 41, the medicant or other substance can flow outwardly through openings 42 in the toothbrush head and also through hollow bristles 43. This toothbrush head can be comprised solely of hollow bristles 43, of a mixture of hollow bristles 43 and regular bristles 44 or solely with regular bristles 44. In the instance where the brush head 40 will be comprised solely of hollow bristles 43, there is no need also for openings 42 in the brush head. In that case, the delivery of the medicants or substances will solely be to the hollow bristles. In the embodiment where there are both hollow bristles and regular bristles, it is optional to also have openings 42 in the brush head. In such an instance, the number and size of such openings 42 will be dependent upon the amount of medicant or other substance which is to be delivered. In the embodiment where the bristles are to be standard bristles 44, it is then necessary to have at least one opening 42 and preferably a plurality of such openings. In that way, an effective amount of medicant or other substance can be delivered. The number and size of the openings will be dependent on the medicant to be delivered and the rate at which it is to be delivered.

The openings 42 will generally be of a diameter of from about 0.1 to 2.5 millimeters. The actual opening diameter will depend on the number of openings and the substance to be delivered. The hollow bristles 43 can have passageways of a diameter of about 0.001 to 0.1 millimeters. The objective is to have the diameter as small as possible so that the bristle with retain its flexibility, but yet of a sufficient diameter so as to be able to deliver the substance from the cartridge.

Figure 6:
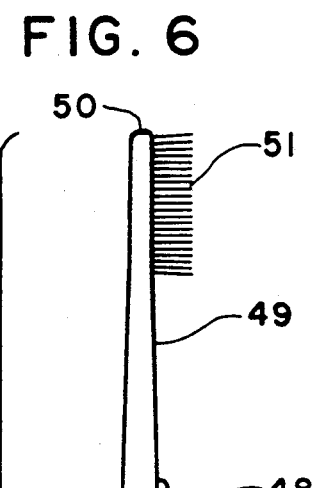
FIG. 6 is a side elevational view of the applicator with a brush attachment.

FIG. 6 discloses a related embodiment for a present pressurized applicator when it is to be used primarily as a toothbrush. In this embodiment, the handle 46 contains an opening 47 into which the pressurized cartridge will be inserted. Once inserted, the pressurized cartridge will have its stem extending upwardly into the valve actuator as shown in FIG. 1. The valve actuator will be activated as in FIG. 1 by means of depressing switch 48. Upon being actuated, pressurized fluid will flow upwardly through delivery section 49 which has a conduit passing therethrough. The medicant or other substance is then delivered up into the brush head 50 of the pressurized applicator. The medicant or other substance will then flow outwardly into the bristle area 51 of the bush in the same manner as has been described in FIG. 5. That is, there can be utilized regular bristles, hollow bristles or a mixture of regular bristles and hollow bristles. Further, there can be openings in the bristle area of the brush head so that medicant can be delivered directly down into the bristle area. In this embodiment, the pressurized applicator will be used primarily in the form of a toothbrush. In contrast, the pressurized applicator of FIGS. 1 through 5 will utilize a replaceable unit at the end of the delivery section.

The pressurized applicator can be constructed out of any known materials. The body housing and the delivery section will be constructed from a plastic, and preferably a thermoset plastic. The periodontal tip and the toothbrush heads that are used can be of any known structure. The pressurized cartridge will be constructed of either an opaque or transparent plastic material. Essentially any material can be utilized for the pressurized cartridge as long as it can withstand at least about 50 psi.

A useful pressurized cartridge is one which has a vapor tap valve. A vapor tap valve is of a type which introduces vapor into the liquid that is to be discharged. In a typical valve of this type, a dip tube projects to near the bottom of the cartridge. This dip tube communicates with a liquid-vapor mixing chamber at the neck portion of the cartridge. Also communicating with this vapor mixing chamber are one or more apertures in the neck of the cartridge. The cartridge containing this vapor tap valve can be used in essentially any orientation. In the upright orientation the dip tube delivers liquid while the neck apertures deliver vapor to the liquid-vapor mixing chamber. In an inverted position, the neck apertures will deliver liquid to the liquid-vapor mixing chamber while the dip tube delivers vapor. The mixing of the liquid and vapor in the cartridge head produces the aerosol. Valves of this type are available from various sources and are used in other products.

In order to use the present pressure application, it is only necessary for the user to determine the medicant or other substance that is desired to be used, and also whether a toothbrush head, a periodontal tip head or some other applicator means should be utilized. If the periodontal tip is to be utilized, the delivery section and the tip are inserted into the oral cavity with the tip extending down into the periodontal pocket area. Once inserted, the trigger is then actuated so that a dosage of the medicant or other substance can be delivered to the periodontal pocket area. A releasing of the trigger actuator will cause the flow of medicant or other substance to cease. When there is to be utilized a toothbrush head on the pressurized applicator, it is only required to choose the toothbrush head that is desired to be used and this toothbrush head attached to the delivery section. Then, during the cleaning of the teeth, or at a time subsequent thereto, the trigger can be actuated so as to deliver a given amount of medicant or other substance to the oral cavity.

What is claimed is:

1. An oral hygiene device comprising a replaceable pressurized cartridge fitted into one end of a body housing, said body housing having at the other end means to deliver a substance to a particular region of the oral cavity, said body housing having a fitment means which is actuated by a trigger, one end of said fitment means receiving said replaceable pressurized cartridge and the other end of said fitment means connected by a conduit to said means to deliver a substance to a particular region of said oral cavity, said replaceable pressurized cartridge having a vapor tap valve whereby said replaceable pressurized cartridge can deliver said substance from the top or bottom of said replaceable pressurized cartridge depending on the orientation of said oral hygiene device.

2. An oral hygiene device as in claim 1 wherein said replaceable pressurized cartridge serves as part of the handle of said oral hygiene device.

3. An oral hygiene device as in claim 1 wherein said substance in said replaceable pressurized cartridge is under a pressure of at least about 20 psi.

4. An oral hygiene device as in claim 1 wherein said replaceable pressurized cartridge has at least one projection and said body housing has at least one recess to accept said at least one projection.

5. An oral hygiene device as in claim 1 wherein said replaceable pressurized cartridge has threads on the exterior surface thereof which mate with internal threads on the inner surface of said body housing so as to maintain said replaceable pressurized cartridge fitted onto said body housing.

6. An oral hygiene device as in claim 1 including at least one coupling arm on said fitment means which extends over a projecting dispensing valve stem on said replaceable pressurized cartridge, said fitment means having an internal opening of a greater diameter to accept said dispensing valve and a decreased diameter passage against which the projecting dispensing valve on said replaceable pressurized cartridge contacts, whereby when said fitment means is pushed downwardly said dispensing valve stem is pushed downwardly to actuate a valve in said replaceable pressurized cartridge.

7. An oral hygiene device as in claim 6 wherein said trigger pivots and contacts said at least one contact arm on said fitment.

8. An oral hygiene device as in claim 6 wherein said trigger forms a part of the body housing.

9. An oral hygiene device as in claim 6 wherein said means to deliver a substance to a particular region of the oral cavity consists of an elongated rigid conduit having on the end thereof a tip for applying said substance to the margin between teeth and gums.

10. An oral hygiene device as in claim 6 wherein said means to deliver a substance to a particular region of the oral cavity consists of an elongated rigid conduit having on the end thereof a plurality of bristles and opening means to provide said substance to the region of the bristle.

11. An oral hygiene device as in claim 6 wherein said means to deliver a substance to a particular region comprises a plurality of hollow bristles for the delivery of medicants and other substances from the brush head.

12. An oral hygiene device as in claim 1 wherein said trigger forms a part of the body housing.

13. An oral hygiene device as in claim 1 wherein said means to deliver a substance to a particular region of the oral cavity consists of an elongated rigid conduit having on the end thereof a tip for applying said substance to the margin between teeth and gums.

14. An oral hygiene device as in claim 1 wherein said means to deliver a substance to a particular region of the oral cavity consists of an elongated rigid conduit having on the end thereof a plurality of bristles and opening means to provide said substance to the region of the bristle.

15. An oral hygiene device as in claim 1 wherein said means to deliver a substance to a particular region comprises a plurality of hollow bristles for the delivery of medicants and other substances from the brush head.

* * * * *